US010836704B2

(12) United States Patent
Schroeter et al.

(10) Patent No.: US 10,836,704 B2
(45) Date of Patent: Nov. 17, 2020

(54) METHOD FOR PRODUCING ETHANOLAMINES AND/OR ETHYLENEAMINES

(71) Applicant: BASF SE, Ludwigshafen am Rhein (DE)

(72) Inventors: Marie Katrin Schroeter, Ludwigshafen am Rhein (DE); Alvaro Gordillo, Heidelberg (DE); Andrei-Nicolae Parvulescu, Ludwigshafen am Rhein (DE); Johann-Peter Melder, Ludwigshafen am Rhein (DE); Carlos Lizandara Pueyo, Ludwigshafen am Rhein (DE); Juergen Bechtel, Heidelberg (DE); Thomas Heidemann, Ludwigshafen am Rhein (DE); Stephan A. Schunk, Heidelberg (DE); Ulrich Mueller, Ludwigshafen am Rhein (DE)

(73) Assignee: BASF SE (DE)

( * ) Notice: Subject to any disclaimer, the term of this patent is extended or adjusted under 35 U.S.C. 154(b) by 0 days.

(21) Appl. No.: 16/469,782

(22) PCT Filed: Dec. 7, 2017

(86) PCT No.: PCT/EP2017/081851
§ 371 (c)(1),
(2) Date: Jun. 14, 2019

(87) PCT Pub. No.: WO2018/108698
PCT Pub. Date: Jun. 21, 2018

(65) Prior Publication Data
US 2020/0079725 A1 Mar. 12, 2020

(30) Foreign Application Priority Data

Dec. 15, 2016 (EP) .................................... 16204482

(51) Int. Cl.
*C07C 209/16* (2006.01)
*B01J 23/80* (2006.01)
*B01J 37/03* (2006.01)
*C07C 213/02* (2006.01)
*C07C 211/10* (2006.01)
*C07C 215/08* (2006.01)

(52) U.S. Cl.
CPC ............ *C07C 209/16* (2013.01); *B01J 23/80* (2013.01); *B01J 37/035* (2013.01); *C07C 213/02* (2013.01); *B01J 2523/13* (2013.01); *B01J 2523/15* (2013.01); *B01J 2523/17* (2013.01); *B01J 2523/22* (2013.01); *B01J 2523/23* (2013.01); *B01J 2523/25* (2013.01); *B01J 2523/27* (2013.01); *B01J 2523/48* (2013.01); *C07C 211/10* (2013.01); *C07C 215/08* (2013.01)

(58) Field of Classification Search
None
See application file for complete search history.

(56) References Cited

U.S. PATENT DOCUMENTS

| 3,137,730 | A |   | 6/1964  | Fitz-William |              |
|-----------|---|---|---------|--------------|--------------|
| 3,270,059 | A |   | 8/1966  | Winderl et al. |            |
| 4,111,840 | A |   | 9/1978  | Best         |              |
| 4,434,300 | A | * | 2/1984  | Deeba .................. | C07C 209/16 564/479 |
| 4,994,622 | A | * | 2/1991  | Fong ........................ | B01J 23/80 564/478 |
| 5,248,827 | A | * | 9/1993  | Hara ........................ | B01J 23/83 546/184 |
| 5,362,700 | A | * | 11/1994 | Doumaux, Jr. .......... | B01J 27/18 502/208 |

(Continued)

FOREIGN PATENT DOCUMENTS

| CN | 102190588 A | 9/2011  |
| CN | 102233272 A | 11/2011 |

(Continued)

OTHER PUBLICATIONS

Segawa (Effect of dealumination of mordenite by acid leaching for selective synthesis of ethylenediamine from ethanolamine, Applied Catalysis A: General 194-195, 2000, p. 309-317) (Year: 2000).*
International Preliminary Examination Report for PCT/EP2017/081851 dated Mar. 13, 2019 with Applicant amendments for WIPO specified grammatical errors.

(Continued)

*Primary Examiner* — Amy C Bonaparte
(74) *Attorney, Agent, or Firm* — Faegre Drinker Biddle & Reath LLP

(57) ABSTRACT

Preparing ethanolamines/ethyleneamines in the presence of an amination catalyst prepared by reducing a calcined catalyst precursor containing one or more metals of groups 8, 9, 10 and/or 11 and low basicity achieved by: a) coprecipitating catalyst precursor and active composition additionally contains alkali metals or alkaline earth metals; b) the catalyst precursor is prepared by impregnating a support material or precipitative application onto a support material containing alkali metals, Be, Ca, Ba, Sr, hydrotalcite, chrysotile or sepiolite; c) the catalyst precursor is prepared by impregnating a support material or precipitative application onto a support material and the active composition of the catalyst support contains one or more of alkali metals and alkaline earth metals; d) the catalyst precursor is calcined at temperatures of 600° C. or more; or e) the catalyst precursor is prepared by a combination of a) and d), b) and d), or c) and d).

14 Claims, No Drawings

(56) References Cited

U.S. PATENT DOCUMENTS

| | | | |
|---|---|---|---|
| 6,525,222 | B2 | 2/2003 | Nouwen et al. |
| 7,405,327 | B2 | 7/2008 | Haese et al. |
| 7,700,806 | B2 | 4/2010 | van Cauwenberge et al. |
| 9,174,201 | B2 | 11/2015 | Ernst et al. |
| 2007/0232833 | A1* | 10/2007 | Haese ............... C07C 209/16 564/472 |

FOREIGN PATENT DOCUMENTS

| | | |
|---|---|---|
| DE | 1172268 B | 6/1964 |
| EP | 198699 B1 | 9/1989 |
| EP | 1106600 A2 | 6/2001 |
| WO | WO-2005110969 A1 | 11/2005 |
| WO | WO-2007093514 A1 | 8/2007 |
| WO | WO-2010031719 A1 | 3/2010 |

OTHER PUBLICATIONS

International Preliminary Examination Report for PCT/EP2017/081851 dated Mar. 26, 2019 with finalized Applicant amendments.
International Search Report for PCT/EP2017/081851 dated Mar. 5, 2018.
Written Opinion of the International Searching Authority for PCT/EP2017/081851 dated Mar. 5, 2018.
Carl Von Ossietzky, "Reaktionskinetische Untersuchungen zur metallkatalysierten Aminierung von Ethylenglykol in der flüssigen Phase", University of Oldenburg, Mar. 17, 2000, 89 pages.
European Search Report for EP Patent Application No. 16204482.0, dated May 26, 2017, 3 pages.

* cited by examiner

METHOD FOR PRODUCING ETHANOLAMINES AND/OR ETHYLENEAMINES

CROSS-REFERENCE TO RELATED APPLICATIONS

This application is a national stage application (under 35 U.S.C. § 371) of PCT/EP2017/081851, filed Dec. 7, 2017, which claims benefit of European Application No. 16204482.0, filed Dec. 15, 2016.

The present invention relates to a process for preparing ethanolamines and/or ethyleneamines.

Two processes are generally employed for industrial scale preparation of ethylenediamine (EDA). Firstly, EDA can be prepared by reaction of 1,2-dichloroethane with ammonia with elimination of HCl (EDC process). A further industrial scale process for preparation of EDA is the reaction of monoethanolamine (MEA) with ammonia in the presence of amination catalysts (MEA process).

As an alternative to the established processes, EDA can also be prepared by reaction of monoethylene glycol (MEG) with ammonia.

Such a process would have various advantages. One advantage is the good availability of MEG compared to MEA.

MEA is prepared on the industrial scale by reaction of ethylene oxide (EO) and ammonia. What is generally formed is a reaction mixture comprising, as well as MEA, also higher ethanolamines such as diethanolamine (DEOA) and triethanolamine (TEOA). These by-products have to be separated from MEA by a separate distillation step. Ethylene oxide is a highly flammable gas that can form explosive mixtures with air. The handling of EO is correspondingly complex. The preparation of MEA thus requires a technically complex EO plant with downstream purifying distillation.

By contrast, MEG can be produced either on the basis of petrochemical raw materials or on the basis of renewable raw materials. By petrochemical means, MEG is likewise prepared from EO by reaction with water. In the same way as in the reaction of EO with ammonia, it is not possible in the reaction of EO with water to prevent MEG that has already formed from reacting with EO to give by-products such as di- and triethylene glycol. The selectivity for MEG is about 90% and is thus, however, distinctly higher than the selectivity for MEA, which is generally 70-80%. However, the Shell omega process once again distinctly increased the selectivity for MEG—to about 99%. In the omega process, EO is reacted with $CO_2$ to give ethylene carbonate which, in the second step, is selectively hydrolyzed to MEG.

MEG can also be prepared via the synthesis gas route, for example by oxidative carbonylation of methanol to give dimethyl oxalate and subsequent hydrogenation thereof. Thus, a further possible petrochemical raw material for the preparation of MEG is also natural gas.

Alternatively, MEG can also be prepared from renewable raw materials, such as corn or sugarcane, by fermentation to ethanol, followed by dehydration to ethene and subsequent reaction with oxygen to give ethylene oxide.

Owing to the many production variants, the availability of MEG is generally high, which generally has a positive effect on raw material costs.

The prior art discloses that the reaction of MEG with ammonia to give EDA can be effected either in the liquid phase or in the gas phase.

An overview of the metal-catalyzed amination of MEG in the liquid phase is given in the Diplom thesis "Reaktionskinetische Untersuchungen zur metallkatalysierten Aminierung von Ethylenglykol in der flüssigen Phase" [Studies of Reaction Kinetics of the Metal-Catalyzed Amination of Ethylene Glycol in the Liquid Phase] by Carsten Wolfgang Ihmels ("Reaktionskinetische Untersuchungen zur metallkatalysierten Aminierung von Ethylenglykol in der flüssigen Phase", Diplom thesis from the Carl von Ossietzky University of Oldenburg dated Mar. 17, 2000). Ihmels describes a multitude of further reactions and side reactions that can occur in the amination of MEG, for example the formation of di- and triethanolamine, disproportionation, nitrile formation, carbonyl condensation and fragmentation reactions. Condensation and disproportionation in the case of dihydric alcohols can ultimately also lead to the formation of oligomers, such as diethylenetriamine (DETA), triethylenetetramine (TETA) and polymers. An important further side reaction is cyclization. For instance, diethanolamine or DETA can react further to give piperazine (PIP). Higher temperatures promote dehydrogenation, which follows on from the cyclization, to give aromatics. Thus, the reaction of MEG with ammonia gives a broad product spectrum, some products in the product spectra being of greater commercial interest than others. For instance, the commercial demand for EDA, DETA and TETA is higher than that for PIP or aminoethylethanolamine (AEEA). The object of many studies in the reaction of MEG with ammonia was therefore to find catalysts and reaction conditions that lead to an advantageous product spectrum.

Ihmels himself studied the conversion of MEG over supported cobalt/silicon dioxide catalysts. Amination to give the desired MEA and EDA target product was unsuccessful. Instead, high-polymeric reaction products were formed. Under milder conditions, still with incomplete conversion of MEG, the target products MEA and EDA were obtained in low yields. The main products were oligomeric compounds.

U.S. Pat. No. 4,111,840 discloses the reaction of MEG with ammonia and hydrogen at pressures of 500 to 5000 psig (about 34 to 340 bar) over supported Ni/Re catalysts. Supported silica/alumina catalysts having a surface area of 60 $m^2/g$ led to better results here than supported silica/alumina catalysts having a specific surface area of 150 $m^2/g$.

U.S. Pat. No. 3,137,730 discloses the reaction of MEG with ammonia in the liquid phase at temperatures of 200-300° C. and pressures above 1000 psig (about 69 bar) over Cu/Ni catalysts.

DE 1 172 268 discloses the conversion of ethylene glycol over catalysts comprising at least one of the metals Cu, Ag, Mn, Fe, Ni and Co. In one example, MEG was reacted with ammonia at 180° C. and a pressure of 300 bar in the presence of hydrogen over a Co catalyst.

WO 2007/093514 discloses a two-stage process for preparing EDA, wherein, in the first process stage, the amination is conducted over a hydroamination catalyst up to an MEA conversion of not more than 40% and, in the second process stage, a supported shaped Ru/Co catalyst body having small geometry is used and the second stage is conducted at a temperature at least 10° C. higher than the first process stage.

As an alternative to the liquid phase, the reaction of MEG with ammonia and hydrogen can also be effected in the gas phase. Advantages of the gas phase reaction over the reaction in the liquid phase is that the reaction can be effected at lower reaction pressures. This can lead to a reduction in capital costs.

However, there is generally a considerable difference in the reaction characteristics of catalysts in the gas phase and liquid phase, and so it is generally impermissible to apply conclusions from the reaction characteristics of MEG in the liquid phase to the reaction characteristics of MEG in the gas phase.

The amination of MEG in the gas phase is described, for example, in the Chinese applications CN 102 190 588 and 102 233 272.

For instance, CN 102 190 588 discloses the one-stage conversion of MEG and ammonia in the presence of Cu catalysts. According to the description, the reaction pressure is within a range from 3 to 30 bar. The reaction temperature is in the range from 150 to 350° C.

A further application (CN 102 233 272) discloses the reaction of MEG with ammonia in the gas phase over catalysts that include Cu and Ni as main constituents and Zr, Zn, Al, Ti, Mn and Ce as secondary component. However, the composition of the reaction mixtures obtained was not disclosed.

It was an object of the present invention to develop a heterogeneous catalyst for the amination of MEG in the gas phase that shows adequate activity and selectivity in the conversion of MEG to MEA and/or EDA.

More particularly, the formation of products of value, i.e. those ethanolamines or ethyleneamines with a high commercial significance, especially MEA and EDA, was to be promoted and the formation of cyclic ethyleneamines, especially PIP, and higher ethanolamines, especially AEEA, was to be kept low since the commercial demand for PIP or AEEA is lower than for EDA and MEA.

The object of the present invention was achieved by a process for preparing ethanolamines and/or ethyleneamines in the gas phase by reacting ethylene glycol with ammonia in the presence of an amination catalyst which is prepared by reducing a calcined catalyst precursor comprising an active composition, where the active composition comprises one or more active metals selected from the group consisting of the elements of groups 8, 9, 10 and 11 of the Periodic Table of the Elements and optionally one or more added catalyst elements selected group consisting of the metals and semimetals of groups 3 to 7 and 12 to 17, the element P and the rare earth elements, wherein
   a) the catalyst precursor is prepared by coprecipitation and the active composition additionally comprises one or more basic elements selected from the group consisting of the alkali metals and alkaline earth metals; or
   b) the catalyst precursor, as well as the active composition, additionally comprises a support material and is prepared by impregnating the support material or precipitative application onto the support material and the support material comprises one or more basic elements selected from the group consisting of the alkali metals, Be, Ca, Ba and Sr or one or more minerals selected from the group consisting of hydrotalcite, chrysotile and sepiolite; or
   c) the catalyst precursor, as well as the active composition, additionally comprises a support material and is prepared by impregnating the support material or precipitative application onto the support material and the active composition of the catalyst support comprises one or more basic elements selected from the group consisting of the alkali metals and the alkaline earth metals;
   d) the catalyst precursor is calcined at temperatures of 600° C. or more; or
   e) the catalyst precursor is prepared by a combination of variants a) and d) or by a combination of variants b) and d) or by a combination of variants c) and d).

The following abbreviations are used above and hereinafter:
AEEA: aminoethylethanolamine
AEP: aminoethylpiperazine
DETA: diethylenetriamine
EDA: ethylenediamine
EO: ethylene oxide
EDC: ethylene dichloride
HEP: hydroxyethylpiperazine
MEA: monoethanolamine
MEG: monoethylene glycol
PEHA: pentaethylenehexamine
PIP: piperazine
TEPA: tetraethylenepentamine
TETA: triethylenetetramine Amination catalysts The process of the invention for preparing ethanolamines and/or ethyleneamines by reaction of MEG with $NH_3$ is effected in the presence of amination catalysts.

Amination catalysts used in the process according to the invention are those that are prepared by reducing calcined catalyst precursors:
Acidity:

Preference is given to using calcined catalyst precursors which, after the calcination, have an acidity of 0.2 mmol $NH_3$/g or less, measured by the method of temperature-programmed desorption of ammonia ($NH_3$-TPD).

More preferably, the catalyst precursors have an acidity of 0.1 mmol $NH_3$/g or less and most preferably an acidity of 0.04 mmol $NH_3$/g or less.

It has been found that, surprisingly, amination catalysts that are obtained by reducing catalyst precursors which have an acidity within the preferred range, and have high selectivity for the linear amination products MEA and EDA, while the selectivity for the cyclic amination product PIP and the higher ethanolamine AEEA is low. A measure of this effect is the selectivity quotient SQ which is defined as the quotient of the sum total of the selectivities of MEA and EDA and the sum total of the selectivities of PIP and AEEA (SQ=(S(MEA)+S(EDA))/(S(PIP)+S(AEEA))). The achievement of a high selectivity quotient SQ is industrially advantageous since the market demand for the linear amination products MEA and EDA and their linear homologs, such as DETA and TETA, is higher than the demand for PIP or AEEA.

It has also been found that amination catalysts that are obtained by reducing amination catalysts with an acidity in the preferred range form a lower level of unwanted by-products. Unwanted by-products are, for example, gaseous breakdown products or insoluble or sparingly soluble oligomers and polymers based on MEA and EDA. The formation of both types of by-products leads to a reduction in the carbon balance and hence to a reduction in the economic viability of the process. The formation of sparingly soluble or insoluble by-products can lead to deposition on the amination catalysts which reduces the activity of the amination catalysts.

In the context of the present invention, the acidity of the catalyst precursors is measured after the last calcination step and before any subsequent optional shaping step.

The acidity is measured by temperature-programmed desorption (TPD). TPD is an experiment in which the non-steady-state, temperature-dependent desorption rate of ammonia from the catalyst surface is monitored and plotted as a function of temperature (desorption curve). The area under the desorption curve indicates the amount of ammonia which is bound on the catalyst precursor by acidic sites on the surface. This is normalized to the amount of catalyst precursor weighed in. TPD is measured in a flow apparatus that preferably consists of glass. In general, between 10 and 500 mg of the catalyst precursor are introduced into the flow apparatus. Prior to the actual TPD experiment, the catalyst precursor is heated in an inert gas stream (He) to 50° C. for 2 hours in order to remove residual moisture present and volatile contaminations. Subsequently, an inert gas stream having a proportion by volume of 10% by volume of ammonia in He is passed over the catalyst precursor in order to saturate the surface of the catalyst with ammonia. The passage of ammonia is generally effected for about 2 hours at a temperature of 50° C. Thereafter, the catalyst precursor is once again purged with pure inert gas at a temperature of 50° C. for another 3 hours in order to remove unbound ammonia. After the purge, the catalyst precursor is heated up from 50° C. to 650° C. at a heating rate of 5 K/min. During the heating, an inert gas (He) is passed over the catalyst precursor at a flow rate of 50 cm$^3$/min. Desorbed ammonia is discharged via the inert gas stream and detected quantitatively with a mass spectrometer, and plotted as a function of temperature as the desorption curve. An example of a suitable apparatus for conducting the TPD is the Autochem II 2920 from Micromeritics GmbH. Achieving the preferred acidity The preferred acidity of the catalyst precursors can be achieved in accordance with the invention in that
  a) the catalyst precursor is prepared by coprecipitation and the active composition additionally comprises one or more basic elements selected from the group consisting of the alkali metals and alkaline earth metals (embodiment a)); or
  b) the catalyst precursor, as well as the active composition, additionally comprises a support material and is prepared by impregnating the support material or precipitative application onto the support material and the support material comprises one or more basic elements selected from the group consisting of the alkali metals, Be, Ca, Ba and Sr or one or more minerals selected from the group consisting of hydrotalcite, chrysotile and sepiolite (embodiment b)); or
  c) the catalyst precursor, as well as the active composition, additionally comprises a support material and is prepared by impregnating the support material or precipitative application onto the support material and the active composition of the catalyst support comprises one or more basic elements selected from the group consisting of the alkali metals and the alkaline earth metals (embodiment c));
  d) the catalyst precursor is calcined at temperatures of 600° C. or more (embodiment d)); or
  e) the catalyst precursor is prepared by a combination of variants a) and d) or by a combination of variants b) and d) or by a combination of variants c) and d) (embodiment e)).

Catalyst Precursors:

The composition of the catalyst precursors is dependent on the preparation method described hereinafter (coprecipitation or precipitative application or impregnation) and on the corresponding embodiment of the invention.

Composition:

In embodiment a) of the invention, in which the catalyst precursor is prepared by coprecipitation, the catalyst precursor, after the calcination, comprises an active composition comprising
one or more active metals selected from the group consisting of the elements of groups 8, 9, 10 and 11 of the Periodic Table of the Elements; and
one or more basic elements selected from the group consisting of the alkali metals and alkaline earth metals; and
optionally one or more added catalyst elements selected group consisting of the metals and semimetals of groups 3 to 7 and 12 to 17, the element P and the rare earth elements.

In this embodiment of the invention, the catalyst precursor does not comprise any support material. If the precipitation, as described hereinafter, is effected in the presence of a support material, the precipitation is referred to in the context of the present invention as precipitative application.

In embodiment b) of the invention, in which the catalyst precursor is prepared by precipitative application or impregnation, the catalyst precursor, after the calcination, comprises a support material comprising at least one or more basic elements selected from the group consisting of the alkali metals, Be, Ca, Ba and Sr, and
an active composition comprising
one or more active metals selected from the group consisting of the elements of groups 8, 9, 10 and 11 of the Periodic Table of the Elements; and
optionally one or more basic elements selected from the group consisting of the alkali metals and alkaline earth metals; and
optionally one or more added catalyst elements selected group consisting of the metals and semimetals of groups 3 to 7 and 12 to 17, the element P and the rare earth elements.

In embodiment c) of the invention, in which the catalyst precursor is prepared by precipitative application or impregnation, the catalyst precursor, after the calcination, comprises
a support material; and
an active composition comprising
one or more active metals selected from the group consisting of the elements of groups 8, 9, 10 and 11 of the Periodic Table of the Elements; and
one or more basic elements selected from the group consisting of the alkali metals and alkaline earth metals; and
optionally one or more added catalyst elements selected group consisting of the metals and semimetals of groups 3 to 7 and 12 to 17, the element P and the rare earth elements.

In embodiment d) of the invention, in which the catalyst precursor is prepared by coprecipitation, the catalyst precursor comprises an
active composition comprising
one or more active metals selected from the group consisting of the elements of groups 8, 9, 10 and 11 of the Periodic Table of the Elements; and
optionally one or more basic elements selected from the group consisting of the alkali metals and alkaline earth metals; and
optionally one or more added catalyst elements selected group consisting of the metals and semimetals of groups 3 to 7 and 12 to 17, the element P and the rare earth elements.

In embodiment d) of the invention, in which the catalyst precursor is prepared by precipitative application or impregnation, the catalyst precursor comprises
a support material optionally comprising one or more basic elements; and
an active composition comprising
one or more active metals selected from the group consisting of the elements of groups 8, 9, 10 and 11 of the Periodic Table of the Elements; and optionally one or more basic elements selected from the group consisting of the alkali metals and alkaline earth metals; and optionally one or more added catalyst elements selected group consisting of the metals and semimetals of groups 3 to 7 and 12 to 17, the element P and the rare earth elements.

The composition of the catalyst precursors and of the support materials can be measured by means of known methods of elemental analysis, for example of atomic absorption spectrometry (AAS), of atomic emission spectrometry (AES), of X-ray fluorescence analysis (XFA) or of ICP-OES (Inductively Coupled Plasma Optical Emission Spectrometry).

The composition of the catalyst precursors is determined here after the last calcination step and prior to any optional shaping step to give a shaped catalyst body.

Catalytically active metals/catalytically active components;

Irrespective of the preparation method and the embodiment, the catalyst precursor comprises one or more active metals selected from groups 8, 9, 10 and 11 of the Periodic Table. Preferably, the catalyst precursor comprises one or more active metals selected from the group consisting of Fe, Ru, Co, Rh, Ni, Pd, Pt, Ag and Cu.

Most preferably, the catalyst precursor comprises one or more active metals selected from the group consisting of Co, Ni, Ag and Cu.

The catalyst precursor very especially preferably comprises the active metal Cu.

In the case of catalyst precursors comprising Cu as active metal, it was possible to achieve the advantages associated with the reduction in the acidity of the catalyst precursors to a particular degree.

After the calcination, the active metals are generally present in the catalyst precursor in the form of the oxygen compounds of the abovementioned active metals, for example as carbonates, oxides, mixed oxides or hydroxides of the active metals, for example as CoO, NiO, CuO and/or mixed oxides thereof.

The oxygen compounds of the active metals obtained after the calcination, such as the carbonates, oxides, mixed oxides or hydroxides of the active metals, are referred to hereinafter as catalytically active components.

The catalytically active components are generally formed by converting soluble compounds of the active metals or precipitated deposits of the active metals at least partly to the catalytically active components by a calcination, the conversion generally being effected by dewatering and/or breakdown.

In the context of this application, the term "catalytically active components" is used for the abovementioned oxygen-containing metal compounds, but is not supposed to imply that these oxygen compounds are themselves already catalytically active. The catalytically active components generally have catalytic activity in the inventive conversion only after reduction. The catalyst precursors may comprise one or more active metals in the active composition. The catalyst precursor comprises preferably 1 to 3, more preferably 1 to 2 and especially preferably 1 active metal(s).

Irrespective of the number of active metals present in the active composition of the catalyst precursor, in the case of catalyst precursors that are prepared as described hereinafter by coprecipitation, the total amount of the active metals is preferably in the range from 1% to 80% by weight, more preferably in the range from 2.5% to 60% by weight and most preferably in the range from 5% to 50% by weight of active metals, based on the total mass of the catalyst precursor.

Irrespective of the number of active metals present in the active composition of the catalyst precursor, in the case of catalyst precursors that are prepared as described hereinafter by precipitative application or impregnation, the total amount of the active metals is preferably in the range from 1% to 80% by weight, preferably 2.5% to 60% by weight and more preferably in the range from 5% to 50% by weight, based on the total mass of the catalyst precursor.

Added Catalyst Elements/Catalyst Additives:

Irrespective of the production method for the catalyst precursor and the embodiment, the active composition, as well as the active metals, may optionally comprise one or more added catalyst elements.

The added catalyst elements are metals or semimetals selected from groups 3 to 7 and 12 to 17 of the Periodic Table, the element P and the rare earth metals.

In the catalyst precursor, the added catalyst elements are generally in the form of their oxygen compounds, for example of carbonates, oxides, mixed oxides or hydroxides of the added catalyst elements. Carbonates, oxides, mixed oxides and hydroxides of the added catalyst elements are referred to hereinafter as catalyst additives.

In general, the catalyst additives are converted to the catalyst additives by a calcination from soluble compounds of the added catalyst elements or precipitates of the added catalyst elements, the conversion generally being effected by dewatering and/or decomposition.

Preferred added catalyst elements are Zr, Zn, Ce, La, Y, Mn and Ti.

Very particularly preferred added catalyst elements are Y, Ce, La, Ti, Zr and Zn.

In the case of catalyst precursors that comprise Y, Ce, La, Ti, Zr and/or Zn as an added catalyst element, it was possible to achieve the advantages associated with the reduction in the acidity of the catalyst precursors to a particular degree.

The catalyst precursors may comprise one or more added catalyst elements in the active composition. The catalyst precursor comprises preferably 1 to 4, more preferably 1 to 3 and especially preferably 1 to 2 added catalyst element(s).

Irrespective of the number of active metals present in the active composition of the catalyst precursor, in the case of catalyst precursors that are prepared as described hereinafter by coprecipitation, the total amount of the added catalyst elements is preferably in the range from 1% to 80% by weight, more preferably in the range from 2.5% to 60% by weight and most preferably in the range from 5% to 50% by weight of added catalyst elements, based on the total mass of the catalyst precursor.

Irrespective of the number of added catalyst elements present in the active composition of the catalyst precursor, in the case of catalyst precursors that are prepared as described hereinafter by precipitative application or impregnation, the total amount of the added catalyst elements is preferably in the range from 1% to 80% by weight, preferably 2.5% to 60% by weight and more preferably in the range from 5% to 50% by weight, based on the total mass of the catalyst precursor.

Basic Elements/Basic Components:

In the claimed embodiments a) and c) and in preferred embodiments of the claimed variants b) and d), the active composition additionally comprises one or more basic elements selected from the group of the alkali metals and alkaline earth metals.

It has been found that, surprisingly, catalyst precursors comprising at least one basic element selected from the group of the alkali metals and alkaline earth metals in the active composition have lower acidity and show the aforementioned advantages in the amination of MEG.

Preferably, the active composition of the catalyst precursor comprises one or more basic elements selected from the group consisting of Li, Na, K, Rb, Mg, Ca and Ba.

More preferably, the active composition of the catalyst precursor comprises one or more basic elements selected from the group consisting of K, Mg, Ca, Cs and Ba.

Most preferably, the active composition of the catalyst precursor comprises the element Ca. After the calcination, these basic elements are generally present in the catalyst precursor in the form of their oxygen compounds, such as their oxides, mixed oxides or carbonates. The oxygen compounds of the basic elements obtained after the calcination are referred to hereinafter as basic components.

The catalyst precursors may comprise one or more basic elements in the active composition. The catalyst precursor preferably comprises 1 to 3, more preferably 1 to 2 and especially preferably 1 basic element(s) in the active composition.

Irrespective of the number of basic elements present in the active composition of the catalyst precursor, in the case of catalyst precursors that are prepared as described hereinafter by coprecipitation, the total amount of the basic elements is preferably in the range from 1% to 80% by weight, more preferably in the range from 2.5% to 60% by weight and most preferably in the range from 5% to 50% by weight of basic elements, based on the total mass of the catalyst precursor.

Irrespective of the number of basic elements present in the active composition of the catalyst precursor, in the case of catalyst precursors that are prepared as described hereinafter by precipitative application or impregnation, the total amount of the basic elements is preferably in the range from 1% to 80% by weight, more preferably in the range from 2.5% to 60% by weight and most preferably in the range from 15% to 50% by weight of basic elements, based on the total mass of the catalyst precursor.

Support Material:

In the case of catalysts that are prepared by precipitative application or impregnation, the catalyst precursor comprises one or more support materials as well as the active composition. The support materials are a solid, generally a solid with a high surface area.

The active composition may be applied to the support material, for example by precipitative application of sparingly soluble precursors of the catalytically active components or by precipitative application of sparingly soluble precursors of the catalyst additives or by precipitative application of sparingly soluble precursors of the basic components or by impregnation of the support material with soluble compounds of the active metals or of the added catalyst elements or of the basic elements.

Further preferred catalyst supports are oxides of the added catalyst elements Al, Ti, Zn, Zr and Si or mixtures thereof, for example aluminum oxide (gamma, delta, theta, alpha, kappa, chi or mixtures thereof), titanium dioxide (anatase, rutile, brookite or mixtures thereof), zinc oxide, zirconium dioxide, silicon dioxide (such as silica, fumed silica, silica gel or silicates), aluminosilicates, minerals, such as hydrotalcite, chrysotile and sepiolite.

Preferably, the total content of support material based on the total mass of the catalyst precursor is in the range from 30% to 99% by weight, preferably 40% to 95% by weight, and more preferably in the range from 50% to 90% by weight.

Basic Support Materials:

In the claimed embodiment b) and in a preferred variant of embodiments c) and d), the support material comprises one or more basic elements selected from the groups consisting of the alkali metals, Be, Ca, Sr and Ba or one or more minerals selected from the group consisting of hydrotalcite, chrysotile and sepiolite.

It has been found that, surprisingly, the precipitative application of catalytically active components to one of the aforementioned basic support materials or impregnation of the basic support materials mentioned with precursors of the catalytically active compounds affords catalyst precursors with low acidity that have the aforementioned advantages.

More preferably, the support material comprises one or more basic elements selected from the group consisting of Na, K and Ca.

Most preferably, the support material comprises the element Ca.

The support material generally comprises 1 to 3, preferably 1 to 2, more preferably 1, basic element(s).

Irrespective of the number of basic elements, the content of basic elements in the support material, based on the total mass of the support material, is in the range from 1% to 50% by weight, preferably 2% to 40% by weight, and more preferably in the range from 2.5% to 20% by weight.

After the calcination, the basic elements in the support material are generally in the form of their oxides or mixed oxides or carbonates.

Preferred basic support materials are metal oxides prepared by coprecipitation of Zn and Ca, for example those comprising 30-70% by weight of ZnO and 30-70% by weight of CaO.

In a further particularly preferred embodiment, the support material comprising one or more basic elements selected from the groups consisting of the alkali metals, Be, Ca, Sr and Ba or one or more minerals selected from the group consisting of hydrotalcite, chrysotile and sepiolite does not comprise any MgO.

Preferred Compositions:

Very particularly preferred catalyst precursors are prepared by coprecipitation and comprise the active metal Cu.

Very particularly preferred catalyst precursors are prepared by coprecipitation and comprise the active metal Cu and at least one of the added catalyst elements Zr and Zn; especially preferred catalyst precursors are those that comprise 1% to 80% by weight of Cu, 2% to 60% by weight of Zn and 0.1% to 10% by weight of Zr, based in each case on the total mass of the catalyst precursor.

Very particularly preferred catalyst precursors are prepared by coprecipitation and comprise the active metal Cu and the basic element Ca; especially preferred catalyst precursors are those that comprise 2.5% to 60% by weight of Cu and 5% to 50% by weight of Ca, based in each case on the total mass of the catalyst precursor.

Very particularly preferred catalyst precursors are prepared by coprecipitation and comprise the active metal Cu and at least one of the added catalyst elements Zr and Zn and the basic element Ca; especially preferred catalyst precursors are those that comprise 1% to 20% by weight of Cu, 20% to 60% by weight of Zn, 0.1% to 10% by weight of Zr and 10% to 40% by weight of Ca, based in each case on the total mass of the catalyst precursor.

Further particularly preferred catalyst precursors are prepared by precipitative application or impregnation and comprise the active metal Cu; especially preferred catalyst precursors are those that comprise 40% to 95% by weight of support material, such as alumina or silica, and 5% to 60% by weight of Cu, based in each case on the total mass of the catalyst precursor.

Further particularly preferred catalyst precursors are prepared by precipitative application or impregnation and comprise the active metal Cu and at least one of the added elements Zn and Zr; especially preferred catalyst precursors are those that comprise 50% to 90% by weight of support material, such as alumina or silica, and 2.5% to 80% by weight of Cu and 2.5% to 40% by weight of Zn and/or 1% to 20% by weight of Zr, based in each case on the total mass of the catalyst precursor.

Further particularly preferred catalyst precursors are prepared by precipitative application or impregnation and comprise the active metal Cu and a support material comprising one or more basic elements. Especially preferred are those catalyst precursors that comprise, as support material, a mixed oxide of CaO and ZnO (CaO/ZnO), where the proportion of the mixed oxide is preferably 40% to 95% by weight, based on the total mass of the catalyst precursor, and the mixed oxide preferably consists of 30-70% by weight of CaO and 30% to 70% by weight of ZnO.

Further particularly preferred catalyst precursors are prepared by precipitative application or impregnation and comprise the active metal Cu and at least one of the added elements Zn and Zr and a basic support material, especially those catalyst precursors that comprise 40% to 95% by weight, based on the total mass of the catalyst precursor, of the aforementioned mixed oxide composed of 30% to 70% by weight of CaO and 30% to 70% by weight of ZnO. Especially preferred are those catalyst precursors having an elemental composition of 1% to 20% by weight of Cu, 20% to 60% by weight of Zn, 0.1% to 10% by weight of Zr and 10% to 60% by weight of Ca, based in each case on the total mass of the catalyst precursor.

Further particularly preferred catalyst precursors are prepared by precipitative application or impregnation and comprise the active metal Cu and at least one basic element in the active composition; especially preferred catalyst precursors are those that comprise 50% to 90% by weight of support material, such as alumina or silica, and also 2.5% to 70% by weight of Cu and 10% to 70% by weight of Ca, based in each case on the total mass of the catalyst precursor.

Further particularly preferred catalyst precursors are prepared by precipitative application or impregnation and comprise the active metal Cu and at least one of the added elements Zn and Zr and at least one basic element in the active composition; especially preferred catalyst precursors are those that comprise 2.5% to 60% by weight of Cu, 2.5% to 60% by weight of Zn and/or 0.1% to 10% by weight of Zr and 2.5% to 60% by weight of Ca, based in each case on the total mass of the catalyst precursor.

Further particularly preferred catalyst precursors are prepared by precipitative application or impregnation and comprise the active metal Cu and at least one of the added elements Zn and Zr and a basic support material and at least one basic element in the active composition; especially preferred catalyst precursors are those that comprise 2.5% to 60% by weight of Cu, 2.5% to 60% by weight of Zn and/or 0.1% to 10% by weight of Zr and 2.5% to 60% by weight of Ca, based in each case on the total mass of the catalyst precursor.

It has been found that, surprisingly, in the case of catalyst precursors having Cu as active metal and/or Zr and/or Zn as added catalyst element, which have advantages associated with reduced acidity to a particular degree.

As described hereinafter, it is preferred in embodiment (e) that all preferred compositions, as described hereinafter, are calcined at a temperature of 600° C. or more.

Preparation of the Catalyst Precursors:

The catalyst precursors can be prepared by known processes, for example by precipitation reactions (e.g. coprecipitation or precipitative application) or impregnation.

Precipitation Reactions:

Coprecipitation:

Catalyst precursors can be prepared by joint precipitation (coprecipitation) of all their components. For this purpose, one or more soluble compounds of the corresponding active metals and optionally one or more soluble compounds of the added catalyst elements in a liquid is admixed with a precipitant while heating and stirring until the precipitation is complete.

The liquid used is generally water.

Useful soluble compounds of the active metals typically include the corresponding metal salts, such as the nitrates, chlorides, sulfates, carboxylates, especially the acetates, or nitrates, of the aforementioned metals.

The soluble compounds of the added catalyst elements that are used are generally water-soluble compounds of the added catalyst elements, for example the water-soluble nitrates, chlorides, sulfates, carboxylates, especially the acetates or nitrates.

The soluble compounds of the basic elements that are used are generally water-soluble compounds of the basic elements, for example the water-soluble nitrates, sulfates, carboxylates, especially the acetates or nitrates.

Precipitative Application:

Catalyst precursors can also be prepared by precipitative application.

Precipitative application is understood to mean a preparation method in which one or more support materials are suspended in a liquid and then soluble compounds of the active metals, such as soluble metal salts of the active metals, and optionally soluble compounds of the added catalyst elements are added, and these are then applied by precipitative application to the suspended support by addition of a precipitant (described, for example, in EP-A2-1 106 600, page 4, and A. B. Stiles, Catalyst Manufacture, Marcel Dekker, Inc., 1983, page 15).

The soluble compounds of the active metals, added catalyst elements and basic elements that are used are generally water-soluble compounds of the active metals, added catalyst elements and basic elements, for example the water-soluble nitrates, chlorides, sulfates, carboxylates, especially the acetates or nitrates.

The support material is generally in the form of powder or spall.

The size of the particles is generally in the range from 50 to 2000 μm, preferably 100 to 1000 μm and more preferably 300 to 700 μm.

The support material may already be in the form of a shaped body (as described hereinafter).

When the support material is in the form of a shaped body, the support material preferably has one of the geometries described hereinafter.

The liquid used, in which the support material is suspended, is typically water.

Precipitation Reactions—General:

Typically, in the precipitation reactions, the soluble compounds are precipitated as sparingly soluble or insoluble, basic salts by addition of a precipitant.

The precipitants used are preferably alkalis, especially mineral bases, such as alkali metal bases. Examples of precipitants are sodium carbonate, sodium hydroxide, potassium carbonate or potassium hydroxide.

The precipitants used may also be ammonium salts, for example ammonium halides, ammonium carbonate, ammonium hydroxide or ammonium carboxylates.

The precipitation reactions can be conducted, for example, at temperatures of 20 to 100° C., particularly 30 to 90° C., especially at 50 to 70° C.

The precipitates obtained in the precipitation reactions are generally chemically inhomogeneous and generally comprise mixtures of the oxides, oxide hydrates, hydroxides, carbonates and/or hydrogencarbonates of the metals or semimetals used. With regard to the filterability of the precipitates, it may prove to be favorable for them to be aged—meaning that they are left to themselves for a certain time after precipitation, optionally under hot conditions or with air being passed through.

Impregnation:

The catalyst precursors can also be prepared by impregnating support materials with soluble compounds of the active metals, added catalyst elements and basic elements (impregnation).

The support materials that are used in the impregnation may be used, for example, in the form of powders or shaped bodies, such as strands, tablets, spheres or rings. Support material suitable for fluidized bed reactors is preferably obtained by spray drying.

The abovementioned support materials can be impregnated by the customary processes (A. B, Stiles, Catalyst Manufacture—Laboratory and Commercial Preparations, Marcel Dekker, New York, 1983), for example by applying a salt of the active metals or added catalyst elements in one or more impregnation stages.

Useful salts of the active metals, of the added catalyst elements and of the basic elements generally include water-soluble salts such as the carbonates, nitrates, carboxylates, especially the nitrates, acetates or chlorides, of the corresponding active metals, added catalyst elements and basic elements, which are generally converted at least partly to the corresponding oxides or mixed oxides under the conditions of the calcination.

The impregnation can also be effected by the "incipient wetness method", in which the support material is moistened with the impregnation solution up to a maximum of saturation, according to its water absorption capacity. Alternatively, impregnation can be effected in supernatant solution.

In the case of multistage impregnation processes, it is appropriate to dry and optionally to calcine between individual impregnation steps. Multistage impregnation should be employed advantageously when the support material is to be contacted with salts in a relatively large amount.

For application of multiple active metals and/or added catalyst elements and/or basic elements to the support material, the impregnation can be effected simultaneously with all salts or in any sequence of the individual salts in succession.

Workup of the Catalyst Precursors:

The impregnated catalyst precursors obtained by these impregnation methods or the precipitates obtained by the precipitation methods are typically processed by separating them from the liquid in which the impregnation or precipitation has been conducted, and washing, drying, calcining and optionally conditioning and subjecting them to a shaping process.

Separation and Washing:

The impregnated catalyst precursors or the precipitates obtained by the precipitation methods are generally separated from the liquid in which the catalyst precursors were prepared and washed.

Processes for separating and washing the catalyst precursors are known, for example, from the article "Heterogenous Catalysis and Solid Catalysts, 2. Development and Types of Solid Catalysts", in Ullmann's Encyclopedia of Industrial Chemistry (DOI: 10.1002/14356007.o05_002).

The wash liquid used is generally a liquid in which the separated catalyst precursor is sparingly soluble but which is a good solvent for impurities adhering to the catalyst, for example precipitant. A preferred wash liquid is water.

In batch preparation, the separation is generally effected with frame filter presses. The washing of the filter residue with wash liquid can be effected here by passing the wash liquid in countercurrent direction to the filtration direction.

In continuous preparation, the separation is generally effected with rotary drum vacuum filters. The washing of the filter residue is typically effected by spraying the filter residue with the wash liquid.

The catalyst precursor can also be separated off by centrifugation. In general, the washing here is effected by adding wash liquid in the course of centrifuging.

Drying

The catalyst precursor separated off is generally dried.

Processes for drying the catalyst precursors are known, for example, from the article "Heterogenous Catalysis and Solid Catalysts, 2. Development and Types of Solid Catalysts", in Ullmann's Encyclopedia of Industrial Chemistry (DOI: 10.1002/14356007.o05_o02).

The drying is effected here at temperatures in the range from preferably 60 to 200° C., especially from 80 to 160° C. and more preferably from 100 to 140° C., where the drying time is preferably 6 h or more, for example in the range from 6 to 24 h. However, depending on the moisture content of the material to be dried, shorter drying times, for example about 1, 2, 3, 4 or 5 h, are also possible.

The washed catalyst precursor that has been separated off can be dried, for example, in chamber ovens, drum driers, rotary kilns or belt driers.

The catalyst precursor can also be dried by spray-drying a suspension of the catalyst precursor.

Calcination:

According to the invention, the catalyst precursors are calcined.

In general, the catalyst precursors are calcined after the drying.

During the calcination, thermally labile compounds of the active metals or added catalyst elements, such as carbonates, hydrogencarbonates, nitrates, chlorides, carboxylates, oxide hydrates or hydroxides, are at least partly converted to the corresponding oxides and/or mixed oxides.

The temperature at which the calcination is effected is dependent on the preparation and composition of the catalyst.

If the active composition of the catalyst precursor comprises a basic element (embodiment a) and c)), the calcination is generally effected at a temperature in the range from 250 to 1200° C., preferably 300 to 1100° C. and especially from 500 to 1000° C.

If neither the active composition of the catalyst precursor after the calcination nor the catalyst support comprises a basic element (this is possible, for example, in embodiment d)), the calcination is effected at a temperature of 600° C. or more, preferably 750° C. or more and more preferably 900° C. or more. In this embodiment, the temperatures are preferably in the range from 600 to 1200° C., more preferably 750 to 1100° C. and most preferably in the range of 900–1000° C.

In embodiment e) of the invention, however, the calcination is also effected at a temperature of 600° C. or more, preferably 750° C. or more and more preferably 900° C. or more in the case of catalyst precursors wherein the active composition comprises a basic element (embodiment a) or c)) and in the case of catalyst precursors comprising a support material with a basic element (embodiment b)). This corresponds to the combination of embodiments a) with d), or b) with d), or c) with d). In these embodiments too, the temperatures are preferably in the range from 600 to 1200° C., more preferably 750 to 1100° C. and most preferably in the range of 900–1000° C.

The calcination can be effected under any suitable gas atmosphere, preference being given to air and/or air mixtures, such as lean air. The calcination alternatively be effected in the presence of hydrogen, nitrogen, helium, argon and/or steam or mixtures thereof.

The calcination is generally effected in a muffle furnace, a rotary kiln and/or a tunnel kiln, the calcination time preferably being 1 h or more, more preferably in the range from 1 to 24 h and most preferably in the range from 2 to 12 h.

Shaped Body:

The catalyst precursors are preferably used in the form of powder or spall. In that case, the particles preferably have a size in the range from 50 to 2000 µm, more preferably 100 to 1000 µm and especially preferably 300 to 700 µm.

However, the catalysts or catalyst precursors are also used with preference in the process of the invention in the form of shaped bodies.

Suitable shaped bodies are shaped bodies having any geometry or shape. Preferred shapes are tablets, rings, cylinders, star extrudates, wagonwheels or spheres, particular preference being given to tablets, rings, cylinders, spheres or star extrudates. Very particular preference is given to the cylinder shape.

In the case of spheres, the diameter of the sphere shape is preferably 20 mm or less, more preferably 10 mm or less, even more preferably 5 mm or less and especially preferably 3 mm or less.

In a preferred embodiment, in the case of spheres, the diameter of the sphere shape is preferably in the range from 0.1 to 20, more preferably 0.5 to 10 mm, even more preferably 1 to 5 mm and especially preferably 1.5 to 3 mm.

In the case of strands or cylinders, the ratio of length:diameter is preferably in the range from 1:1 to 20:1, more preferably 1:1 to 14:1, even more preferably in the range from 1:1 to 10:1 and especially preferably in the range from 1:2 to 6:1.

The diameter of the strands or cylinders is preferably 20 mm or less, more preferably 15 mm or less, even more preferably 10 mm or less and especially preferably 3 mm or less.

In a preferred embodiment, the diameter of the strands or cylinders is preferably in the range from 0.5 to 20 mm, more preferably in the range from 1 to 15 mm, most preferably in the range from 1.5 to 10 mm.

In the case of tablets, the height h of the tablet is preferably 20 mm or less, more preferably 10 mm or less, even more preferably 5 mm or less and especially preferably 3 mm or less.

In a preferred embodiment, the height h of the tablet is preferably in the range from 0.1 to 20 mm, more preferably in the range from 0.5 to 15 mm, even more preferably in the range from 1 to 10 mm and especially preferably in the range from 1.5 to 3 mm.

The ratio of height h (or thickness) of the tablet to the diameter D of the tablet is preferably 1:1 to 1:5, more preferably 1:1 to 1:2.5, even more preferably 1:1 to 1:2 and especially preferably 1:1 to 1:2.

The shaped body used preferably has a bulk density (to EN ISO 6) in the range from 0.1 to 3 kg/l, preferably from 1.5 to 2.5 kg/l and especially preferably 1.7 to 2.2 kg/l.

Shaping:

In the production of the catalyst precursors by impregnation or by precipitative application, preference is given to using support materials that already have the above-described preferred geometry of the shaped bodies.

Catalyst precursors that do not have the above-described preferred shaped body geometry can be subjected to a shaping step.

In the course of shaping, the catalyst precursors are generally conditioned by adjusting them to a particular particle size by grinding.

After the grinding, the conditioned catalyst precursor can be mixed with further additives, such as shaping aids, for example graphite, binders, pore formers and pasting agents, and processed further to give shaped bodies.

Standard processes for shaping are described, for example, in Ullmann [Ullmann's Encyclopedia Electronic Release 2000, chapter: "Catalysis and Catalysts", pages 28-32] and by Ertl et al. [Ertl, Knözinger, Weitkamp, Handbook of Heterogeneous Catalysis, VCH Weinheim, 1997, pages 98 ff.].

Standard processes for shaping are, for example, extrusion, tableting, i.e. mechanical pressing, or pelletizing, i.e. compaction by circular and/or rotating movements.

The shaping operation can give shaped bodies with the abovementioned geometry.

The shaping can alternatively be effected by spray-drying a suspension of the catalyst precursor.

The conditioning or shaping is generally followed by a heat treatment. The temperatures in the heat treatment typically correspond to the temperatures in the calcination.

Reduction/Passivation:

According to the invention, the conversion of MEG and ammonia is effected over a reduced catalyst precursor. The reduction generally converts the catalyst precursor to the catalytically active form thereof.

The reduction of the catalyst precursors can be effected as described hereinafter prior to the contacting with the MEG and ammonia reactants, or it can be effected in situ in the same reactor in which the reaction of MEG with ammonia is also effected. Between the reduction of the catalyst precursors and prior to the contacting of the catalysts with the reactants, the catalysts can additionally be passivated. If the catalysts are passivated as described hereinafter, the catalysts are activated again prior to the contacting or during the contacting with the reactants.

The reduction of the catalyst precursor can be conducted at elevated temperature in an agitated or unagitated reduction furnace.

The reducing agent used is typically hydrogen or a hydrogen-comprising gas.

The hydrogen is generally used in technical grade purity. The hydrogen can also be used in the form of a hydrogen-comprising gas, i.e. in mixtures with other inert gases, such as nitrogen, helium, neon, argon or carbon dioxide. In a preferred embodiment, hydrogen is used together with nitrogen, where the proportion by volume of hydrogen is preferably in the range from 1% to 50%, more preferably 2.5% to 30% and especially preferably 5% to 25% by volume. The hydrogen stream can also be recycled into the reduction as cycle gas, optionally mixed with fresh hydrogen and optionally after removal of water by condensation.

The catalyst precursor is preferably reduced in a reactor in which the shaped bodies are arranged as a fixed bed. Particular preference is given to reducing the catalyst precursor in the same reactor in which the subsequent reaction of MEG with $NH_3$ is effected.

In addition, the catalyst precursor can be reduced in a fluidized bed reactor in the fluidized bed.

The catalyst precursor is generally reduced at reduction temperatures of 50 to 600° C., especially from 100 to 500° C., more preferably from 150 to 450° C.

The partial hydrogen pressure is generally from 1 to 300 bar, especially from 1 to 200 bar, more preferably from 1 to 100 bar, the pressure figures here and hereinafter relating to the pressure measured in absolute terms.

The duration of the reduction is preferably 1 to 20 hours, and more preferably 3 to 15 hours.

During the reduction, a solvent can be supplied in order to remove water of reaction formed and/or in order, for example, to be able to heat the reactor more quickly and/or to be able to better remove the heat during the reduction. The solvent here may also be supplied in supercritical form.

Suitable solvents may be used the solvents described above. Preferred solvents are water; ethers such as methyl tert-butyl ether, ethyl tert-butyl ether, dioxane or tetrahydrofuran. Particular preference is given to water or tetrahydrofuran. Suitable solvents likewise include suitable mixtures.

The shaped body thus obtained, after reduction, can be handled under inert conditions. The shaped body can preferably be handled and stored under an inert gas such as nitrogen, or under an inert liquid, for example an alcohol, water or the product of the particular reaction for which the catalyst is used. In that case, it may be necessary to free the catalyst of the inert liquid prior to commencement of the actual reaction.

Storage of the catalyst under inert substances enables uncomplicated and nonhazardous handling and storage of the shaped body.

After reduction, the shaped body can also be contacted with an oxygen-comprising gas stream such as air or a mixture of air with nitrogen.

This gives a passivated shaped body. The passivated shaped body generally has a protective oxide layer. This protective oxide layer simplifies the handling and storage of the catalyst, such that, for example, the installation of the passivated shaped body into the reactor is simplified. A passivated shaped body is preferably reduced as described above by treatment of the passivated catalyst with hydrogen or a hydrogen-comprising gas prior to contacting with the reactants. The reduction conditions generally correspond to the reduction conditions which are employed in the course of reduction of the catalyst precursors. The activation generally removes the protective passivation layer.

Reactants:

According to the invention, the inventive conversion of ethylene glycol (EG) and ammonia ($NH_3$) is effected in the presence of the reduced or activated amination catalysts in the gas phase.

Ethylene Glycol:

As ethylene glycol is preferably industrial ethylene glycol having a purity of at least 98%, and most preferably ethylene glycol having a purity of at least 99% and most preferably of at least 99.5%.

The ethylene glycol used in the process can be prepared from ethylene obtainable from petrochemical processes. For instance, in general, ethene is oxidized in a first stage to ethylene oxide, which is subsequently reacted with water to give ethylene glycol. The ethylene oxide obtained can alternatively be reacted with carbon dioxide in what is called the omega process to give ethylene carbonate, which can then be hydrolyzed with water to give ethylene glycol. The omega process features a higher selectivity for ethylene glycol since fewer by-products, such as di- and triethylene glycol, are formed.

Ethene can alternatively be prepared from renewable raw materials. For instance, ethene can be formed by dehydration from bioethanol.

Ammonia:

According to the invention, ethylene glycol is reacted with ammonia,

The ammonia used may be conventional commercially available ammonia, for example ammonia with a content of more than 98% by weight of ammonia, preferably more than 99% by weight of ammonia, preferably more than 99.5% by weight, in particular more than 99.8% by weight of ammonia.

Hydrogen:

The process of the invention is preferably effected in the presence of hydrogen.

The hydrogen is generally used in technical grade purity. The hydrogen can also be used in the form of a hydrogen-comprising gas, i.e. with additions of other inert gases, such as nitrogen, helium, neon, argon or carbon dioxide. Hydrogen-comprising gases used may, for example, be reformer offgases, refinery gases etc., if and as long as these gases do not comprise any catalyst poisons for the catalysts used, for example CO. However, preference is given to using pure hydrogen or essentially pure hydrogen in the process, for example hydrogen having a content of more than 99% by weight of hydrogen, preferably more than 99.9% by weight of hydrogen, more preferably more than 99.99% by weight of hydrogen, especially more than 99.999% by weight of hydrogen.

Reaction in the Gas Phase:

According to the invention, ethylene glycol is reacted with ammonia and an amination catalyst in the gas phase.

In the context of the present invention, "reaction in the gas phase" means that the reaction conditions, such as pressure and temperature, are adjusted such that ethylene glycol and $NH_3$ are present in the gas phase and flow around the amination catalyst in gaseous form.

Reactors:

Suitable reactors for the gas phase reaction are generally tubular reactors and fluidized bed reactors. The catalyst may be arranged as a moving bed or fixed bed in the tubular reactors.

Particular preference is given to reacting ethylene glycol with $NH_3$ in a tubular reactor in which the amination catalyst is arranged in the form of a fixed bed.

In a further particular embodiment, ethylene glycol is reacted with ammonia in a fluidized bed reactor.

Reaction Conditions:

Preferably, the reaction of MEG with $NH_3$ in the gas phase is effected at a pressure in the range from 0.05 to 20 MPa, more preferably 0.1 to 10 MPa, even more preferably 0.3 to 5 MPa and especially preferably 0.5 to 3 MPa. In a particularly preferred embodiment, the pressure is in the range from 0.7 to 1.5 MPa.

The temperature is preferably in the range from 120 to 600° C., more preferably in the range from 180 to 500° C., even more preferably in the range from 200 to 350° C. and especially preferably in the range from 220 to 270° C.

Input:

The reactants are preferably supplied to the reactor in gaseous form and contacted with the amination catalyst in gaseous form. For this purpose, the reactants are generally guided through a heat exchanger prior to introduction into the reactor and evaporated. The evaporation can also be effected by a flash evaporation.

The proportion of MEG in the gas stream which is contacted with the amination catalyst is generally in the range of 0.1% to 10% by volume, preferably 0.5% to 7.5% by volume, even more preferably 1% to 6.5% by volume and especially 2.5% to 5% by volume.

The proportion of $NH_3$ in the gas stream which is contacted with the amination catalyst is generally in the range from 5% to 90% by volume, preferably 10% to 80% by volume, even more preferably 25% to 60% by volume and especially 30% to 45% by volume.

The molar ratio of $NH_3$ to MEG is generally in the range from 1:1 to 50:1, preferably 5:1 to 30:1, more preferably 10:1 to 20:1, especially preferably 13:1 to 16:1.

The gas stream which is contacted with the amination catalyst may optionally comprise hydrogen. The proportion of $H_2$ in the gas stream which is contacted with the amination catalyst is generally in the range from 0.1% to 70% by volume, preferably 0.5% to 50% by volume, more preferably 1% to 40% by volume, even more preferably 2.5% to 35% by volume and especially 5% to 25% by volume.

It is further preferable that the gas stream which is contacted with the amination catalyst comprises an inert gas. Preferred inert gases are noble gases, such as He, Ne, Ar, nitrogen and mixtures thereof. Very particularly preferred inert gases are Ar and nitrogen, or mixtures thereof. The proportion of inert gas in the gas stream which is contacted with the amination catalyst is generally in the range from 5% to 90% by volume, preferably 10% to 80% by volume, even more preferably 25% to 60% by volume and especially 30% to 50% by volume.

In a preferred variant, the gas stream which is contacted with the amination catalyst comprises less than 3% by volume, more preferably less than 0.1% by volume, even more preferably less than 0.005% by volume and especially preferably less than 0.00001% by volume of water.

The gas hourly space velocity (GHSV) which is contacted with the amination catalyst is generally 100 to 30 000 $h^{-1}$, preferably 500 to 20 000 $h^{-1}$, more preferably 1000 to 15 000 $h^{-1}$ and especially preferably 3000 to 8000 $h^{-1}$.

At the catalyst hourly space velocities stated, the conversion of MEG is generally in the range from 5% to 60%, preferably in the range from 10% to 55% and most preferably in the range from 20% to 50%.

Output:

The output from the amination reactor comprises the products of the amination reaction, unconverted reactants, such as ethylene glycol and ammonia, and also hydrogen and water, in gaseous form.

The output from the amination reactor also comprises the corresponding ethanolamines and/or ethyleneamines based on MEG.

The output from the amination reactor preferably comprises MEA and EDA.

The reaction output also preferably comprises higher linear ethyleneamines of the general formula

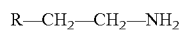

$R-CH_2-CH_2-NH_2$ where R is a radical of the formula $-(NH-CH_2-CH_2)_x-NH_2$ where x is an integer in the range from 1 to 4, preferably 1 to 3 and most preferably 1 to 2. Preferably, the reaction output comprises DETA, TETA and PETA, more preferably DETA and TETA and especially preferably DETA.

The output from the amination reactor may also comprise higher linear ethanolamines of the formula

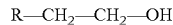

$R-CH_2-CH_2-OH$ where R is a radical of the formula $-(NH-CH_2-CH_2)_x-NH_2$ where x is an integer in the range from 1 to 4, preferably 1 to 3 and most preferably 1 to 2.

One example of a higher linear ethanolamine is AEEA.

The reaction output may also comprise cyclic ethanolamines of the formula

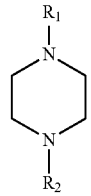

where $R_1$ is a radical of the formula $-(CH_2-CH_2-NH)_x-CH_2-CH_2-OH$ where x is an integer in the range from 0 to 4, preferably 0 to 3 and more preferably 1 to 2, and $R_2$ is independently or simultaneously either H or a radical of the formula $-(CH_2-CH_2-NH)_x-CH_2-CH_2-OH$ where x is an integer in the range from 0 to 4, preferably 0 to 3 and more preferably 1 to 2, or a radical of the formula $-(CH_2-CH_2-NH)_x-CH_2-CH_2-NH_2$ where x is an integer in the range from 0 to 4, preferably 0 to 3 and more preferably 1 to 2.

The reaction output may also comprise cyclic ethyleneamines of the general formula

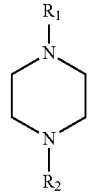

where $R_1$ and $R_2$ may independently or simultaneously be either H or a radical of the formula $-(CH_2-CH_2-NH)_x-CH_2-CH_2-NH_2$ where X is an integer in the range from 0 to 4, preferably 0 to 4 and more preferably 1 to 2.

Examples of cyclic ethyleneamines present in the reaction output are piperazine and AEPIP.

The output preferably comprises 1% to 60% by weight of MEA, 1% to 90% by weight of EDA, 0.1% to 30% by weight of higher cyclic ethyleneamines, such as PIP and AEPIP, 0.1% to 30% by weight of higher linear ethyleneamines, such as DETA, TETA and TEPA.

The output more preferably comprises 10% to 50% by weight of MEA, 25% to 85% by weight of EDA, 0.25% to 10% by weight of cyclic ethyleneamines, such as PIP and AEPIP, 1% to 30% by weight of higher linear ethyleneamines, such as DETA, TETA and TEPA.

The output most preferably comprises 15% to 45% by weight of MEA, 30% to 70% by weight of EDA, 0.5% to 5% by weight of cyclic ethyleneamines, such as PIP and AEPIP, 5% to 25% by weight of higher linear ethyleneamines, such as DETA, TETA and TEPA.

The process of the invention can achieve selectivity quotients SQ of 1.5 or more, preferably 4 or more and more preferably of 8 or more. This means that the product ratio of desired linear ethyleneamines and ethanolamines, such as MEA and EDA, to unwanted cyclic ethyleneamines and unwanted higher ethanolamines, such as PIP and AEEA, can be increased by the process of the invention.

The output from the amination reactor optionally comprises the amination catalyst, which is generally separated from the gaseous components by a suitable apparatus, for example by means of a solids separation which is generally configured as a centrifugal separator (or else cyclone or cyclone separator).

The gaseous output is generally worked up, such that the different components are separated from one another.

For this purpose, the gaseous output is partially condensed, such that hydrogen and any ammonia remain in the gas phase and the other components present in the output are converted to the liquid phase. The gaseous components are generally separated from the liquid components in a gas/liquid separator. The gaseous components can be recycled into the amination reactor individually (after a further workup step) or together.

After hydrogen and any ammonia has been separated off, the output from the amination reactor optionally comprises ammonia, unconverted ethylene glycol, water and the amination products.

Preferably, the output from the amination reactor is separated in two separation sequences, where each separation sequence comprises a multistage distillation. Such a workup is described, for example, in EP-B1-198699. Accordingly, in the first separation sequence, water and ammonia are first separated off and, in the second separation sequence, a separation into unconverted MEG, and MEA, EDA, PIP, DETA, AEEA and higher ethyleneamines. In this case, lower- and higher-boiling components relative to the azeotrope of MEG and DETA are first removed and then the mixture that has been concentrated in MEG and DETA is separated by extractive distillation with triethylene glycol (TEG) as selective solvent into a stream comprising MEG and DETA.

Advantages:

It has been found that, surprisingly, the output from the amination reactor in the process of the invention has a high ratio of MEA and EDA to PIP and AEEA. In addition, it is possible to reduce the amount of unwanted by-products, such as uncondensable breakdown products and higher condensation products. Both by-products can lead to a reduction in the carbon balance. The former case can give rise to volatile breakdown products of low molecular weight. Higher condensation products, by contrast, can be deposited on the catalysts, where they can additionally also be carbonized. This can lower the activity of the catalyst. The achieving of high selectivity quotients SQ is economically advantageous since the demand for linear amination products such as MEA and EDA is higher than the demand for the cyclic compound PIP or for the linear higher ethanolamine AEEA.

The invention is illustrated by the following examples:

Preparation of the Catalyst Precursors

Comparative Example 1: Calcination of the Catalyst Precursor at Low Temperatures 467 g of an aqueous copper nitrate solution (CuO content: 19.3% by weight) and 581.7 g of an aqueous zinc nitrate solution (ZnO content: 17.2% by weight) and 49.3 g of an aqueous zirconium acetate solution ($ZrO_2$ content: 20.3% by weight) were mixed and precipitated with NaOH at a pH of 5 and a temperature of 80° C. After the precipitation, the pH was increased to 8 and the mixture was left at that pH for 15 minutes. Subsequently, the precipitated solids were filtered off and washed. The filter residue was dried at 120° C. for 16 hours. After the drying, the dried pulverulent residue was heated up to 500° C. (heating rate 10 K/min) and calcined at 500° C. for 120 minutes.

The metal content of the catalyst precursor thus obtained was 33% by weight of Cu, 38% by weight of Zn and 3.4% by weight of Zr.

Example 1: Calcination of the Catalyst Precursor at High Temperatures

The preparation was analogous to comparative example 1, except that the dried pulverulent residue was heated up to 900° C. (heating rate 10 K/min) and calcined at 900° C. for 120 minutes.

The metal content of the catalyst precursor thus obtained was 36% by weight of Cu, 41% by weight of Zn and 3.8% by weight of Zr.

Comparative Example 2: Calcination of the Catalyst Precursor at Low Temperatures 103.8 g of copper nitrate solution (CuO content: 19.3% by weight) and 336.9 g of calcium nitrate were mixed with 300 mL of water. Thereafter, 100 g of γ-alumina powder were mixed with water. The metal salt solution prepared beforehand was added to the aqueous alumina suspension. A pH of 5 was established by adding NaOH, which resulted in precipitation. After the precipitation, the pH was increased to 8 and the mixture was left at that pH for 15 minutes. Subsequently, the precipitated solids were filtered off and washed. The filter residue was dried at 120° C. for 16 hours. After the drying, the dried residue was heated up to 500° C. (heating rate 10 K/min) and calcined at 500° C. for 120 minutes.

The metal content of the catalyst precursor thus obtained was 16.8% by weight of Al, 21.4% by weight of Ca and 6.4% by weight of Cu.

Example 2: Calcination of the Catalyst Precursor at High Temperatures

The preparation was analogous to comparative example 2, except that the dried residue was heated up to 900° C. (heating rate 10 K/min) and calcined at 900° C. for 120 minutes.

The metal content of the catalyst precursor thus obtained was 19.9% by weight of Al, 25.5% by weight of Ca and 7.6% by weight of Cu.

Comparative Example 3: Calcination of the Catalyst Precursor at Low Temperatures 200 g of Siliperl AF 125 (spall: 250-500 μm) were impregnated with 152 mL of a metal salt solution having the following composition: 45% by weight of CuO from copper nitrate, 50% by weight of ZnO from zinc nitrate, 5% by weight of ZrO2 from zirconium acetate). The amount of metal salt solution used corresponds to 95% of the maximum water absorption of the catalyst support. After the impregnation, the catalyst precursor was dried at 120° C. for 16 hours. Thereafter, the dried catalyst precursor was heated to 500° C. (heating rate 10 K/min) and calcined at 500° C. for 120 minutes.

temperature was chosen such that the amount of MEG in the gas stream corresponds to the amount specified in table 1.

The gas stream was heated to the temperature specified in table 1 and passed through the reactor at 10 bar.

The gas hourly space velocity (GHSV) was 5000 $h^{-1}$.

The composition of the gas stream was determined by gas chromatography and is reported in table 1.

TABLE 1

|  | Comparative example 1 | Example 1 | Comparative example 2 | Example 2 | Comparative example 3 | Example 3 |
|---|---|---|---|---|---|---|
| T [° C.] | 250 | 250 | 250 | 250 | 250 | 250 |
| % by vol. of H2 | 20 | 20 | 40 | 40 | 20 | 20 |
| % by vol. of NH3 | 40 | 40 | 40 | 40 | 40 | 40 |
| CB % | 80.9 | 93.8 | 96.0 | 98.1 | 89.2 | 96.8 |
| MEG conversion (%) | 48.4 | 18.9 | 13.9 | 8.2 | 16.0 | 6.4 |
| EDA yield (%) | 9.0 | 3.2 | 5.1 | 2.9 | 1.42 | 1.53 |
| MEA yield (%) | 6.5 | 8.4 | 1.6 | 3.1 | 0.61 | 1.32 |
| PIP yield (%) | 8.4 | 0.7 | 2.7 | 0.3 | 1.42 | 0.19 |
| Acidity ($NH_3$ uptake in mmol/g) | 0.044 | 0 | 0.31 | 0.066 | 0.262 | 0.031 |
| Total selectivity S* (%) | 49.3 | 65.0 | 68.0 | 77.3 | 21.5 | 47.3 |
| Selectivity quotient SQ** | 1.08 | 4.49 | 1.8 | 8.5 | 1.01 | 8.18 |

*Total selectivity S = yield (MEA + EDA + DETA + PIP + AEEA)/conversion(MEG) × 100
**Selectivity quotient SQ = yield(EDA + DETA)/yield(AEEA + PIP)

The metal content of the catalyst precursor thus obtained was 10.9% by weight of Cu, 12.6% by weight of Zn and 1.1% by weight of Zr.

Example 3: Calcination of the Catalyst Precursor at High Temperatures

The preparation was analogous to comparative example 3, except that the dried residue was heated up to 900° C. (heating rate 10 K/min) and calcined at 900° C. for 120 minutes.

The metal content of the catalyst precursor thus obtained was 10.9% by weight, 12.8% by weight of Zn and 1.1% by weight of Zr.

Reaction of MEG and $NH_3$

Example 4

The calcined catalyst precursors were tabletted and converted to spall and sieved so as to obtain its size distribution of the particles in the powder of 0.315 to 0.5 mm.

The powder was introduced into a tubular reactor and fixed with two quartz frits.

The diameter of the fixed catalyst bed was 4 mm and the length 80 mm.

The tubular reactor was heated up to the reaction temperature specified in table 1.

Ammonia was evaporated into a gas stream of nitrogen and hydrogen (for hydrogen content see table 1) in a first evaporator. The evaporation temperature was chosen such that the amount of ammonia in the gas stream corresponds to the amount specified in table 1. In a second evaporator, MEG was evaporated into the gas stream. The evaporation In the case of catalyst precursors with identical composition, it was solely through the calcination at higher temperatures that it was possible to distinctly increase the ratio of desired linear products (MEA and EDA) to PIP, measured by the selectivity quotient SQ. It was also possible to improve the carbon balance (CB). The improvement in the carbon balance is an indication that both the formation of low molecular weight breakdown products undetectable by GC and the formation of high molecular weight condensates likewise undetectable by GC have been reduced. Particularly the high molecular weight condensates can lead to deposits on the catalyst that can reduce the activity of the catalyst.

Preparation of the Catalyst Precursors

Comparative Example 5: Catalyst Precursor with No Basic Component 467 g of an aqueous copper nitrate solution (CuO content: 19.3% by weight) and 581.7 g of an aqueous zinc nitrate solution (ZnO content: 17.2% by weight) and 49.3 g of an aqueous zirconium acetate solution ($ZrO_2$ content: 20.3% by weight) were mixed and precipitated with NaOH at a pH of 5 and a temperature of 80° C. After the precipitation, the pH was increased to 8 and the mixture was left at that pH for 15 minutes. Subsequently, the precipitated solids were filtered off and washed. The filter residue was dried at 120° C. for 16 hours. After the drying, the dried pulverulent residue was heated up to 500° C. (heating rate 10 K/min) and calcined at 500° C. for 120 minutes.

The metal content of the catalyst precursor thus obtained was 33% by weight of Cu, 38% by weight of Zn and 3.4% by weight of Zr.

Example 5A: Catalyst Precursor Comprising a Basic Component by Coprecipitation

Procedure analogous to comparative example 4, except with replacement of a portion of the copper nitrate and zirconium acetate by calcium nitrate*4H$_2$O, such that the starting solution used was a mixture of 102.4 g of a copper nitrate solution (CuO content: 19.3% by weight), 558.3 g of a zinc nitrate solution (ZnO content: 17.2% by weight), 336.9 g of calcium nitrate*4H$_2$O in 400 mL of water.

The metal content of the catalyst precursor thus obtained was 6.1% by weight of Cu, 30% by weight of Zn and 21.2% by weight of Ca.

Example 5B: Catalyst Precursor by Impregnation of a Basic Support Material

An impregnation solution was prepared by mixing an aqueous copper nitrate solution (CuO content: 19.3% by weight) and 5 of an aqueous zirconium acetate solution (ZrO$_2$ content: 20.3% by weight), such that the ratio of Cu:Zr in the solution obtained was 90:10.

100 g of a support material (composition: 56% by weight of ZnO; 44% by weight of CaO) (particle size: 315-500 μm) were impregnated with 33.5 mL of the impregnation solution. The impregnated catalyst precursor was dried at 120° C. for 16 hours. After the drying, the dried catalyst precursor was heated up to 500° C. (heating rate 10 K/min) and calcined at 500° C. for 120 minutes.

Example 5C: Catalyst Precursor by Impregnation of a Basic Support Material

The impregnation solution was prepared by mixing copper nitrate and water, such that the theoretical CuO oxide content of the solution was 19.3% by weight.

100 g of a support material (composition: 56% by weight of ZnO; 44% by weight of CaO) (particle size: 315-500 μm) were impregnated with 33.5 mL of the impregnation solution. The further treatment of the catalyst precursor was conducted analogously to example 5B. Reaction of MEG and NH$_3$ Reaction of MEG and NH$_3$ Example 6

The calcined catalyst precursors were conditioned so as to obtain a size distribution of the particles in the powder of 0.315 to 0.5 mm.

The powder was introduced into a tubular reactor and fixed with two quartz frits.

The diameter of the fixed catalyst bed was 4 mm and the length 80 mm.

The tubular reactor was heated up to the reaction temperature specified in table 2.

Ammonia was evaporated into a gas stream of nitrogen and hydrogen (for hydrogen content see table 2) in a first evaporator. The evaporation temperature was chosen such that the amount of ammonia in the gas stream corresponds to the amount specified in table 1. In a second evaporator, MEG was evaporated into the gas stream. The evaporation temperature was chosen such that the amount of MEG in the gas stream corresponds to the amount specified in table 2.

The gas stream was heated to the temperature specified in table 2 and passed through the reactor at 10 bar.

The gas hourly space velocity (GHSV) was 5000 h$^{-1}$.

The composition of the gas stream was determined by gas chromatography and is reported in table 2.

TABLE 2

|  | Comparative example 5 | Example 5A | Example 5B | Example 5C |
|---|---|---|---|---|
| T [° C.] | 250 | 250 | 250 | 250 |
| % by vol. of H2 | 20 | 20 | 20 | 40 |
| CB % | 80.9 | 92.6 | 93.2 | 94.6 |
| MEG conversion (%) | 48.4 | 22.0 | 15.9 | 14.4 |
| EDA yield (%) | 9.0 | 4.5 | 2.9 | 2.7 |
| MEA yield (%) | 6.5 | 8.5 | 5.7 | 5.9 |
| PIP yield (%) | 8.4 | 0.6 | 0.3 | 0.2 |
| Acidity (NH$_3$ uptake in mmol/g) | 0.044 | 0 | 0 | 0 |
| Total selectivity S* (%) | 49.3 | 61.8 | 55.4 | 60.7 |
| Selectivity quotient SQ** | 1.08 | 7.7 | 11.2 | 11.3 |

*Total selectivity S = yield (MEA + EDA + DETA + PIP + AEEA)/conversion(MEG) × 100
**Selectivity quotient SQ = yield(EDA + DETA)/yield(AEEA + PIP)

It is apparent from the table that catalyst precursors that have been obtained in accordance with the invention by impregnating a basic support material or that have been obtained by coprecipitation and comprise a basic component in the active composition lead to a distinct increase in the selectivity quotient SQ in the reaction of MEG with NH$_3$. An increase in the selectivity quotient SQ means that the ratio of the desired linear amination products MEA and EDA has risen significantly in relation to the unwanted amination product PIP. Moreover, the carbon balance is significantly improved. The improvement in the carbon balance is an indication that both the formation of low molecular weight breakdown products undetectable by GC and the formation of high molecular weight condensates likewise undetectable by GC has been reduced. Particularly the high molecular weight condensates can lead to deposits on the catalyst that can reduce the activity of the catalyst.

The invention claimed is:

1. A process for preparing ethanolamines and/or ethyleneamines in the gas phase by reacting ethylene glycol (MEG) with ammonia in the presence of an amination catalyst which is prepared by reducing a calcined catalyst precursor comprising an active composition, where the active composition comprises one or more active metals selected from the group consisting of the elements of groups 8, 9, 10 and 11 of the Periodic Table of the Elements and optionally one or more added catalyst elements selected group consisting of the metals and semimetals of groups 3 to 7 and 12 to 17, the element P and the rare earth elements, wherein
   a) the catalyst precursor is prepared by coprecipitation and the active composition additionally comprises one or more basic elements selected from the group consisting of the alkali metals and alkaline earth metals, and the total amount of the basic elements is in the range from 2.5% to 80% by weight, based on the total mass of the catalyst precursor after calcination; or
   b) the catalyst precursor is prepared by precipitative application or impregnation of the active composition onto a support material, wherein the support material after calcination comprises one or more basic elements selected from the group consisting of the alkali metals, Be, Ca, Ba and Sr or one or more minerals selected from the group consisting of hydrotalcite, chrysotile and sepiolite; or c) the catalyst precursor is prepared by precipitative application or impregnation of the active composition onto a support material and the active composition of the catalyst support after calcination additionally comprises one or more basic elements selected from the group consisting of the alkali metals and the alkaline earth metals, and the total amount of the basic elements is in the range from 2.5% to 80% by weight, based on the total mass of the catalyst precursor after calcination; or d) the catalyst precursor is calcined at temperatures of 900° C. or more; or e) the catalyst precursor is prepared by a combination of variants a) and d) or by a combination of variants b) and d) or by a combination of variants c) and d);

wherein the acidity of the calcined catalyst precursor is less than 0.2 mmol/g $NH_3$, measured by temperature-programmed desorption of ammonia.

2. The process according to claim 1, wherein MEG and $NH_3$ are reacted in the gas phase at a pressure in the range from 0.5 to 3 MPa and at a temperature in the range from 200 to 350° C.

3. The process according to claim 1, wherein the reaction is effected by contacting a gas stream comprising MEG and $NH_3$ in a fixed bed reactor with the amination catalyst, and the gas hourly space velocity (GHSV) which is contacted with the amination catalyst is 1000 to 30 000 $h^{-1}$.

4. The process according to claim 1, wherein ethylene glycol and ammonia are reacted over the amination catalyst in the presence of hydrogen.

5. The process according to claim 4, wherein the proportion by volume of hydrogen in the gas stream which is contacted with the amination catalyst is in the range from 5% to 25% by volume.

6. The process according to claim 1, wherein the catalyst precursor is calcined in variant d) at a temperature in the range from 900 to 1200° C.

7. The process according to claim 6, wherein the catalyst precursor is calcined in variant d) at a temperature in the range from 900 to 1100° C.

8. The process according to claim 1, wherein the catalyst precursor is prepared by variants b) or c) and comprises the active metal Cu.

9. The process according to claim 1, wherein the catalyst precursor comprises one or more added catalyst elements selected from the group consisting of Zr and Zn.

10. The process according to claim 1, wherein the basic elements in variants a) and c) of claim 1 comprise one or more elements selected from the group consisting of K, Mg, Ca, Cs, and Ba and/or wherein the active composition of the catalyst precursor of variant d) further comprises one or more basic elements selected from the group consisting of K, Mg, Ca, Cs, and Ba.

11. The process according to claim 1, wherein the catalyst precursor in variants b) and d) of claim 1 comprises a support material which is a mixed oxide of CaO and ZnO.

12. The process according to claim 1, wherein the catalyst precursor is prepared by precipitative application or impregnation and comprises
  2.5% to 60% by weight of Cu;
  2.5% to 60% by weight of Zn and/or 0.1% to 10% by weight of Zr; and
  2.5 to 60% by weight of Ca,
  based in each case on the total mass of the catalyst precursor after calcination.

13. The process according to claim 11, wherein the catalyst precursor is prepared by precipitative application or impregnation and comprises 40% to 95% by weight, based on the total mass of the catalyst precursor after calcination, of the mixed oxide according to claim 12, and where the composition of the catalyst precursor is 1% to 20% by weight of Cu, 20% to 60% by weight of Zn, 0.1% to 10% by weight of Zr and 10% to 60% by weight of Ca, based in each case on the total mass of the catalyst precursor after calcination.

14. The process according to claim 7, wherein the catalyst precursor is prepared by a combination of variants a) and d) or by a combination of variants b) and d) or by a combination of variants c) and d).

* * * * *